(12) United States Patent
Guzman

(10) Patent No.: US 6,939,380 B2
(45) Date of Patent: Sep. 6, 2005

(54) MOBILE TALAR COMPONENT FOR TOTAL ANKLE REPLACEMENT IMPLANT

(75) Inventor: Jose F. Guzman, Fort Wayne, IN (US)

(73) Assignee: Depuy Products, Inc., Warsaw, IN (US)

( * ) Notice: Subject to any disclaimer, the term of this patent is extended or adjusted under 35 U.S.C. 154(b) by 82 days.

(21) Appl. No.: 10/327,743

(22) Filed: Dec. 23, 2002

(65) Prior Publication Data

US 2004/0122523 A1 Jun. 24, 2004

(51) Int. Cl.⁷ .................................................. A61F 2/42
(52) U.S. Cl. .................................................. 623/21.18
(58) Field of Search .......................... 623/21.18, 21.11, 623/21.12, 21.13, 20.21, 18.11

(56) References Cited

U.S. PATENT DOCUMENTS

| | | | |
|---|---|---|---|
| 3,886,599 A | | 6/1975 | Schlein |
| 3,889,300 A | | 6/1975 | Smith |
| 3,987,500 A | | 10/1976 | Schlein |
| 4,069,518 A | | 1/1978 | Groth, Jr. et al. |
| 4,156,944 A | * | 6/1979 | Schreiber et al. ........ 623/21.18 |
| 4,470,158 A | * | 9/1984 | Pappas et al. ........... 623/20.21 |
| 5,041,139 A | | 8/1991 | Brånemark |
| 5,326,365 A | * | 7/1994 | Alvine .................... 623/21.18 |
| 5,755,801 A | * | 5/1998 | Walker et al. ........... 623/20.21 |
| 5,766,259 A | | 6/1998 | Sammarco |
| 5,824,106 A | * | 10/1998 | Fournol .................. 623/21.18 |
| 6,039,764 A | * | 3/2000 | Pottenger et al. ........ 623/20.32 |
| 6,090,144 A | * | 7/2000 | Letot et al. ............. 623/20.34 |
| 6,183,519 B1 | | 2/2001 | Bonnin et al. |
| 6,296,666 B1 | * | 10/2001 | Gardner .................. 623/20.29 |
| 6,361,564 B1 | * | 3/2002 | Marceaux et al. ....... 623/20.29 |
| 6,409,767 B1 | * | 6/2002 | Perice et al. ............ 623/21.18 |
| 6,443,991 B1 | | 9/2002 | Running |
| 2003/0181985 A1 | * | 9/2003 | Keller et al. ............ 623/21.18 |

FOREIGN PATENT DOCUMENTS

| | | |
|---|---|---|
| DE | 10123124 | 12/2002 |
| WO | WO 0189427 | 11/2001 |

* cited by examiner

*Primary Examiner*—Pedro Philogene

(57) ABSTRACT

An ankle prosthesis includes a tibial device attachable to a tibia. The tibial device has a concave articulating surface. A talar assembly includes a dome portion having a convex articulating surface engaging the concave articulating surface of the tibial device such that the dome portion is pivotable relative to the tibial device. The talar assembly also includes a base portion attachable to a talus. The base portion is pivotable relative to the dome portion.

20 Claims, 8 Drawing Sheets

MOBILE TALAR COMPONENT FOR TOTAL ANKLE REPLACEMENT IMPLANT

BACKGROUND OF THE INVENTION

The present invention relates to prosthetic systems for the replacement of joints or portions thereof. More particularly, the invention concerns an ankle prosthesis system that can be used in the extremities that have experienced bone loss or significant, irreparable bone trauma.

For treatment of various problems with the ankle such as degenerative arthritis and trauma of the ankle, total ankle replacement, or "arthroplasty" is rapidly becoming a common course of action. One method of providing relief to a patient is to replace the articulating surfaces of the ankle, i.e. the inferior articular surface of the tibia and the articular surface of the talus. The inferior articular surface of the tibia is replaced with a concave polymer bearing, and the articular surface of the talus is replaced with a convex metal bearing. The polymer used can be polyethylene, for example. In such replacement, pain relief, increased motion and anatomic reconstruction of the ankle joint are goals of the orthopaedic surgeon.

There are two basic types of ankle replacements: unconstrained meniscal bearing ankle prostheses and semi-constrained fixed bearing ankle prostheses. An example of a semi-constrained fixed bearing ankle prosthesis is the Agility Ankle by DePuy. Semi-constrained fixed bearing ankle prostheses include one articulating interface, i.e., the interface between the concave polymer bearing surface and the convex metal bearing surface. In semi-constrained prostheses, the concave polymer bearing is locked in place relative to the tibia. Further, the convex metal bearing surface is locked in place relative to the talus. Thus, semi-constrained fixed bearing ankle prostheses provide the patient with only a limited amount of ankle movement.

Unconstrained meniscal bearing ankle prostheses, in contrast, include two articulating interfaces, allowing additional degrees of freedom. One articulating interface is between a tibial component and a meniscal bearing. The other articulating interface is between the meniscal bearing and a talar component. Examples of unconstrained meniscal bearing ankle prostheses are the S.T.A.R. prosthesis from Link, and the B-P ankle from Endotech, both of which are loaded from the front of the ankle. There are several problems with such unconstrained ankle prostheses, a few of which will be listed here as examples. First, ankle stability is poor. Specifically, the meniscal polymer bearing can become dislocated. Second, an unconstrained ankle prosthesis cannot be used on patients with excessive varus/valgus misalignment or a soft tissue weakness that affects the alignment or stability of the foot. Third, fibrous tissues tend to encapsulate the bearing, thereby limiting motion. Fourth, the tibial component is known to migrate due to the small amount of bone contact area.

Consequently, there is a need for an ankle prosthesis system that allows greater freedom of movement than does a semi-constrained fixed bearing ankle prosthesis and that does not have the disadvantages of an unconstrained meniscal bearing ankle prosthesis.

SUMMARY OF THE INVENTION

In order to address these needs, the present invention comprises a semi-constrained ankle prosthesis including a talar component that is rotatable relative to the talus, thereby providing the ankle with an additional degree of freedom.

In one form, the subject invention provides an ankle prosthesis including a tibial device attachable to a tibia. The tibial device has a concave articulating surface. A talar assembly includes a dome portion having a convex articulating surface engaging the concave articulating surface of the tibial device such that the dome portion is pivotable relative to the tibial device. The talar assembly also includes a base portion attachable to a talus. The base portion is pivotable relative to the dome portion.

In another form, the subject invention provides an ankle prosthesis including a tibial device attachable to a tibia. A talar assembly includes a dome portion engaging the tibial device such that the dome portion is pivotable relative to the tibial device in a first plane. The talar assembly also includes a base portion attachable to a talus. The base portion is pivotable relative to the dome portion in a second plane substantially perpendicular to the first plane.

In yet another form, the subject invention provides an ankle prosthesis including a tibial device attachable to a tibia. A talar assembly includes a first portion engaging the tibial device such that the first portion is pivotable relative to the tibial device in a first plane. A second portion is attached to a talus of a foot. The second portion is pivotable relative to the first portion in a second plane substantially parallel to a third plane defined by a sole of the foot.

An advantage of the present invention is that the range of motion of the ankle joint in the gait cycle is increased.

Another advantage is that the ability of the talar component to move under and within the tibial component enhances the implant's lifespan by reducing the stress across the ankle joint.

Yet another advantage is that wear of the concave polymer bearing is minimized.

DESCRIPTION OF THE FIGURES

FIG. 7 is a top view of the talar assembly and talus of FIG. 2, illustrating the pivoting of the dome portion relative to the talus.

FIG. 8 is another top view of the talar assembly and talus of FIG. 2, illustrating the pivoting of the dome portion relative to the talus.

Corresponding reference characters indicate corresponding parts throughout the figures.

DESCRIPTION OF THE PREFERRED EMBODIMENTS

Figure 1:
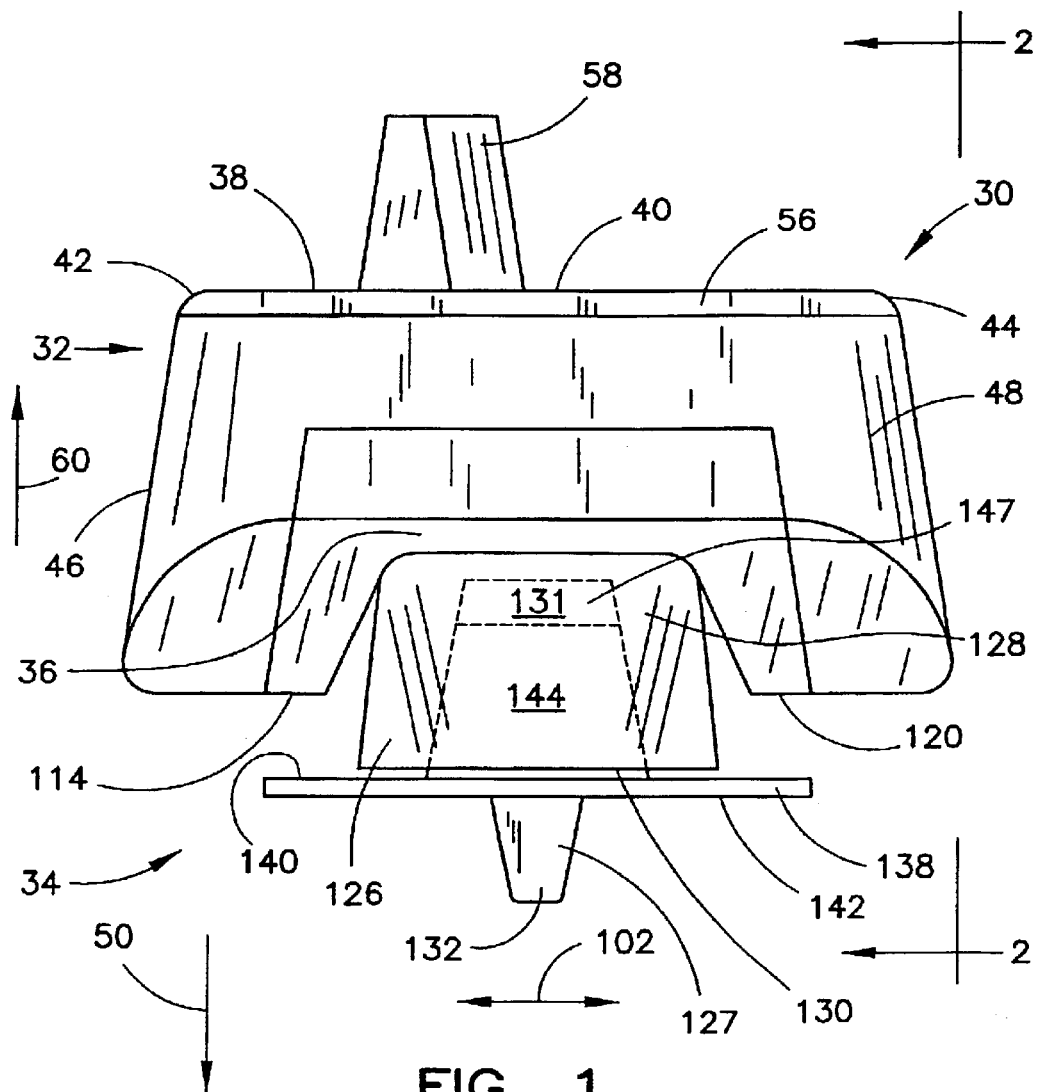
FIG. 1 is a rear view of an ankle replacement or prosthesis in accordance with one embodiment of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, there is depicted one embodiment of the subject invention. Particularly, there is depicted an ankle prosthesis generally designated 30. The ankle prosthesis 30 is for a right ankle. An ankle prosthesis for a left ankle would be a mirror image of the ankle prosthesis 30. The ankle prosthesis 30 is configured for replacement surgery wherein the patient's ankle joint is replaced. The ankle prosthesis 30 includes a talar assembly or component 34 and a tibial device in the form of a tibial assembly or component 32. The tibial assembly 32 and the talar assembly 34 interact to provide flexion and extension of the talus relative to the tibia. According to one inventive aspect of the present invention, the tibial assembly 32 and the talar assembly 34 also interact to allow the talus to pivot relative to the tibia in a plane perpendicular to the plane of flexion and extension, similar to that of a normal ankle. The ankle prosthesis 30 is compact so as to require minimal removal of the patient's bone and tissue.

The tibial assembly 32 includes a bearing component 36 which fits into and is held by a tibial component 38. The tibial component 38 includes a base plate or superior wall 40 having a medial edge 42 and a lateral edge 44. Positioning walls including a medial wall 46 and a lateral wall 48 extend from the medial edge 42 and the lateral edge 44, respectively, in a superior-to-inferior direction 50. Extending from a posterior edge 52 (FIG. 2) of the superior wall 40 in an anterior-to-posterior direction 54 is a triangular extension 56. A projection in the form of a tibial fin 58 extends from the superior wall 40 in an inferior-to-superior direction 60.

The bearing component 36 is formed of a resilient material, such as a polymer or plastic. In particular, the bearing component 36 can be formed of polyethylene. The bearing component 36 includes a concave articulating surface 96 for interfacing with the talar assembly 34. The concave articulating surface 96 faces in the superior-to-inferior direction 50. The concave articulating surface 96 forms an arc from an anterior side 98 to a posterior side 100 such that a cross section of the surface 96 is constant along a medial-lateral axis 102. A medial side portion 114 and a lateral side portion 120 of the bearing component 36 are proximate the medial wall 46 and the lateral wall 48, respectively.

Figure 3:
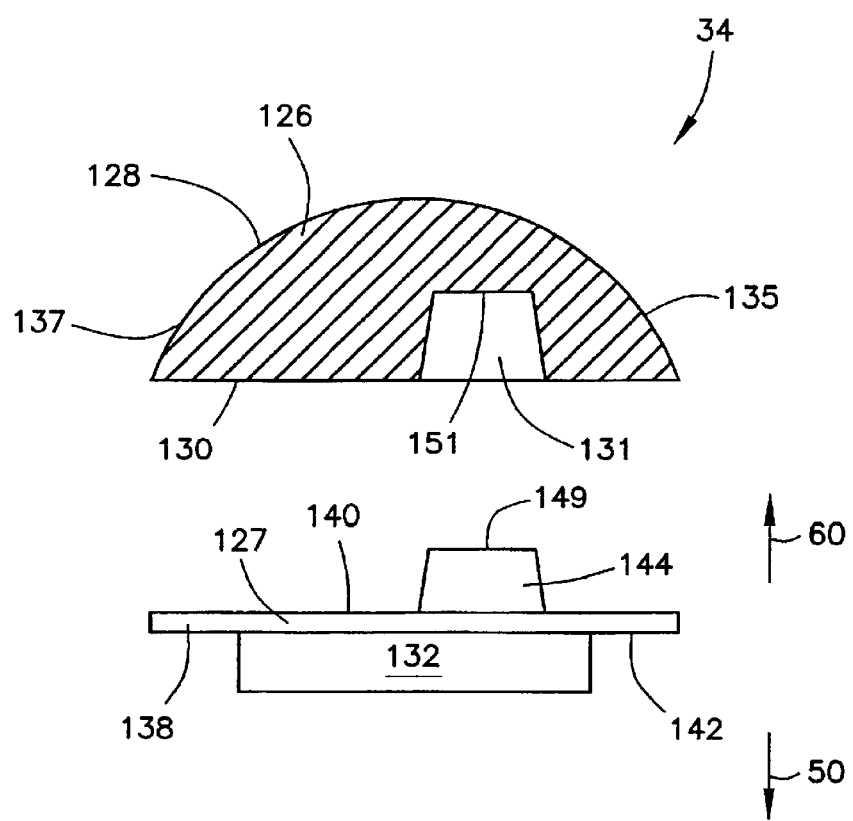
FIG. 3 is an exploded, side, partially sectional view of the talar assembly of FIG. 1.
Figure 4:
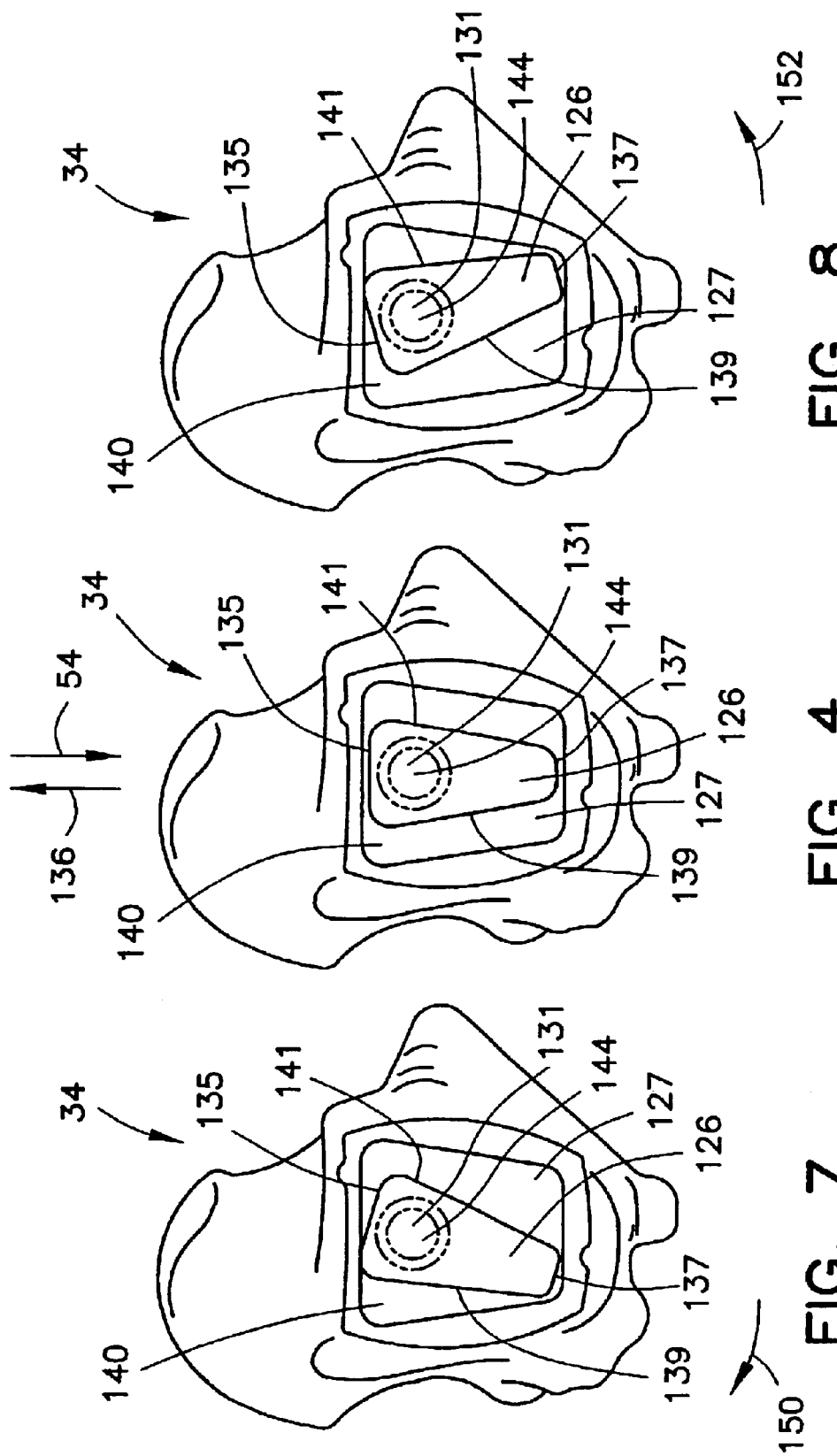
FIG. 4 is a top view of the talar assembly and talus of FIG. 2.

The talar assembly 34 includes a superior portion or dome portion 126 and an inferior portion or base portion 127, as best seen in FIG. 3. The dome portion 126 has a convex articulating surface in the form of an arcuate curving surface 128. The curving surface 128 extends along an arc between an anterior end 135 of the dome portion 126 and a posterior end 137. As best seen in FIG. 4, the dome portion 126 tapers along its arc in the anterior-to-posterior direction 54. That is, the dome portion 126 has a medial side 139 and a lateral side 141 that angle slightly outward from the posterior end 137 to the anterior end 135. A flat underside 130 of the dome portion 126 has a frustoconically-shaped recess 131 therein. In the embodiment shown, the recess 131 is closer to the anterior end 135 of the dome portion 126 than to the posterior end 137.

Figure 2:
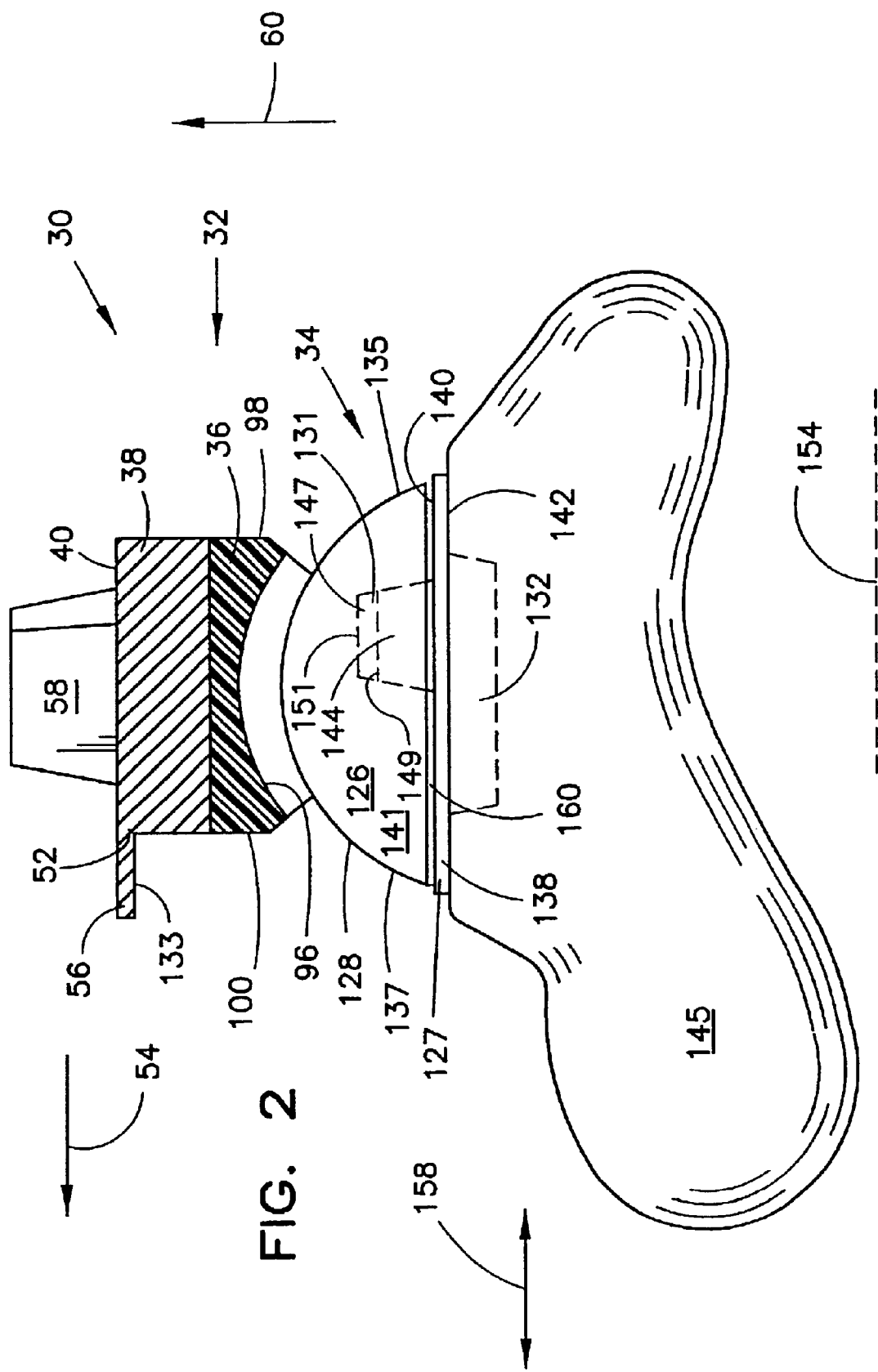
FIG. 2 is a partially sectional, partially exploded side view of the ankle prosthesis along line 2—2 in FIG. 1 with a talar assembly attached to a talus.
Figure 5:
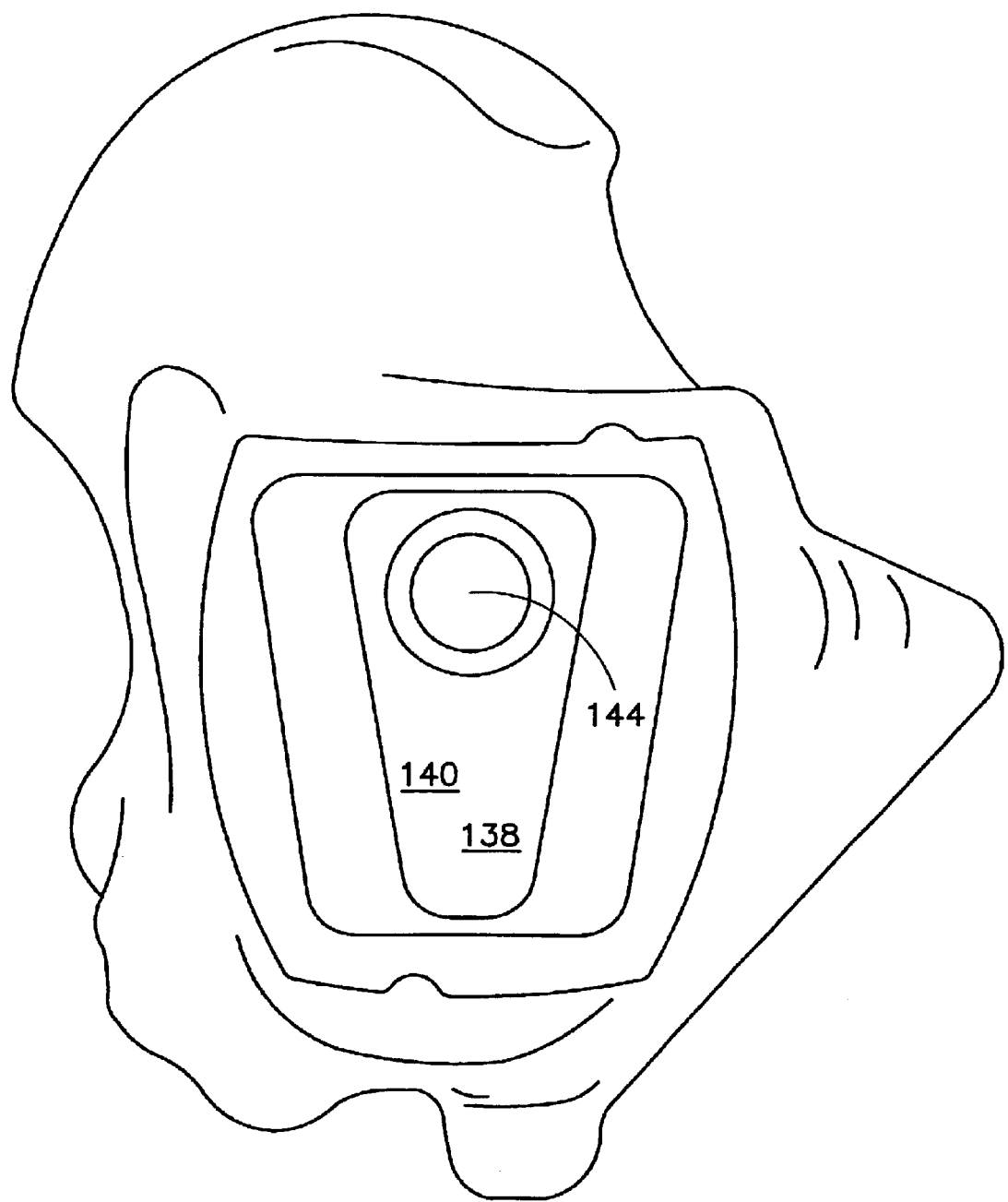
FIG. 5 is a top view of the talus and the base of the talar assembly of FIG. 4.

The base portion 127 has a plate 138 with a superior side 140, best seen in FIG. 5, and an inferior side 142. On the superior side 140 is a frustoconically-shaped projection 144 extending in the inferior-to-superior direction 60 and sized to fit within the recess 131. As shown in FIG. 2, there is a gap 147 between a superior side 149 of the projection 144 and an inferior surface 151 defining the recess 131. However, it is also possible for the superior side 149 of the projection 144 to either touch the inferior surface 151 or be adjacent the inferior surface 151. On the inferior side 142 is a projection in the form of a talar fin 132 extending in the superior-to-inferior direction 50. The talar fin 132 is to be implanted into a talus 145 of a patient's foot.

Figure 6:
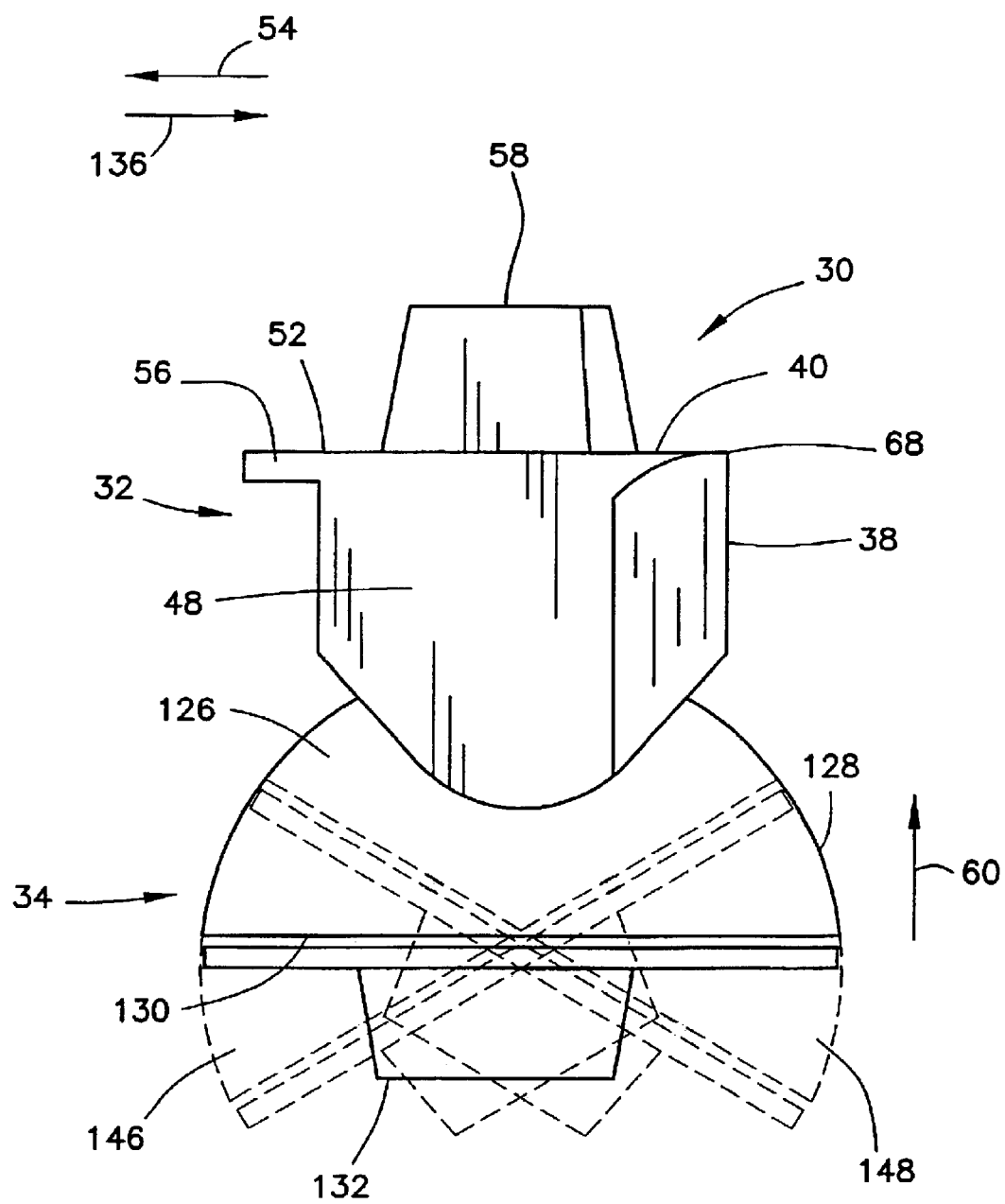
FIG. 6 is a side view of the ankle prosthesis of FIG. 1, illustrating the range of flexion and extension of the talar assembly.

The tapering dome portion 126 of the talar assembly 34 fits in a complementary manner with the tibial bearing component 36. The concave surface 96 of the bearing component 36 fits against the dome portion 126. The side portions 114, 120 of the bearing component 36 engage the sides 139, 141, respectively, of the dome portion 126. The dome portion 126 slides and pivots relative to the tibial device 32. Particularly, the dome portion 126 slides and pivots relative to the bearing component 36 in a plane perpendicular to the medial-lateral axis 102. Thus, relative pivoting motion between the dome portion 126 and the tibial assembly 32 is enabled. The bearing component 36 and the dome portion 126 provide a range of motion of approximately sixty degrees between an extended position 146 and a flexed position 148, as shown in FIG. 6.

Referring again to FIG. 1, it can be seen that the side portions 114, 120 of the bearing component 36 and the walls 46, 48 of the tibial component 38 retain the dome portion 126 from lateral sliding at all positions. The walls 46, 48 provide support to the joint so that the ankle prosthesis 30 remains properly positioned at all times. As best shown in FIG. 4, the dome portion 126 widens slightly in the posterior-to-anterior direction 136. Thus, the wider end 135 is better able to accommodate the recess 131 without loss of structural integrity than is the narrower end 137. The distance between the side portions 114, 120 also widens in a similar manner, which keeps the tibial assembly 32 and the dome portion 126 aligned. The ankle prosthesis 30 pivots at the meeting of the dome portion 126 and the bearing component 36 to provide flexion and extension. The surfaces 96, 128 slide relative to one another and allow pivoting to occur, thereby having a motion and range of motion similar to that of a natural ankle joint.

Figure 9:
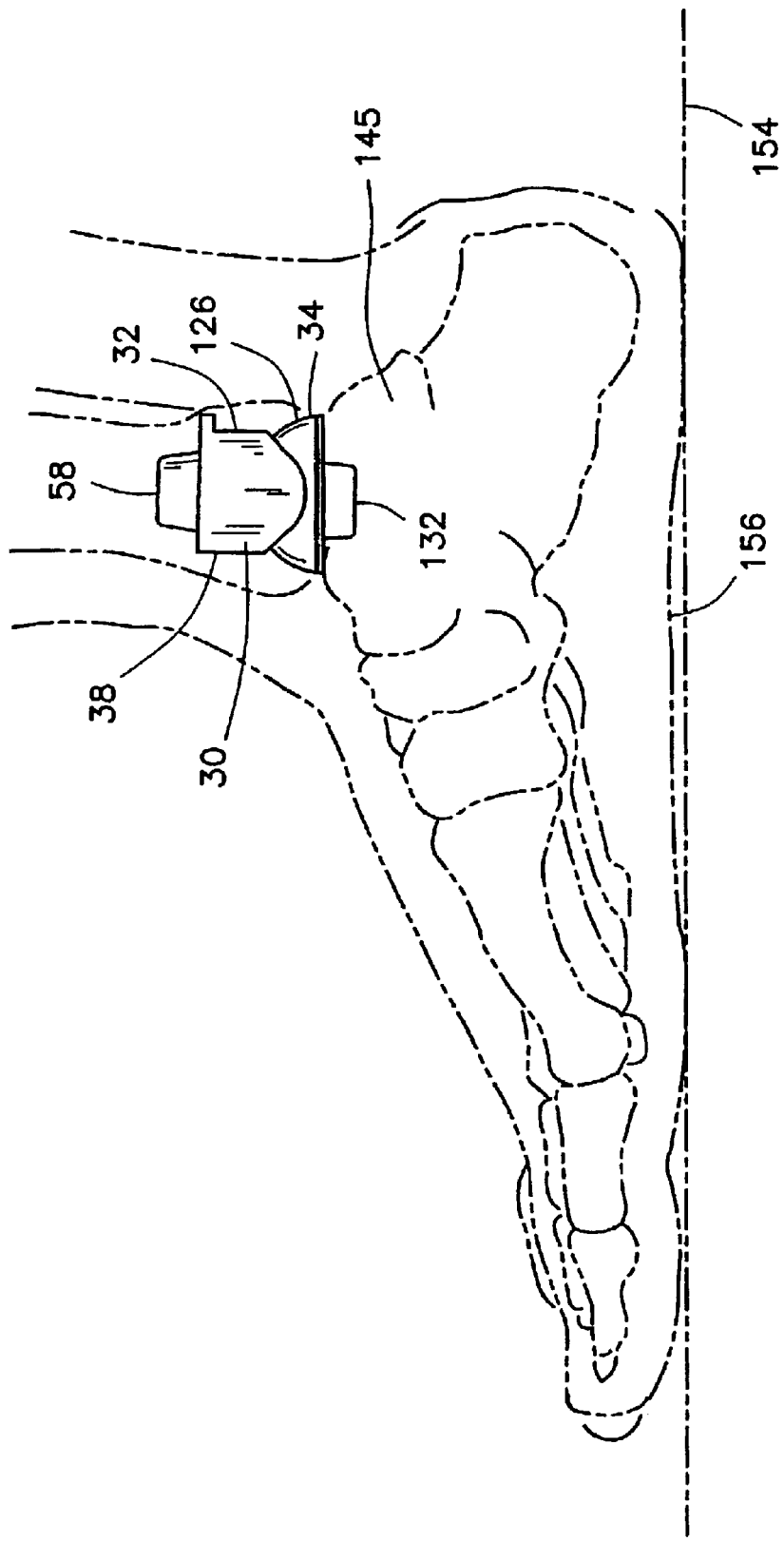
FIG. 9 is a side view of the ankle prosthesis of FIG. 1 implanted in a patient's ankle.

According to an inventive feature of the present invention, the dome portion 126 is pivotable relative to the base portion 127, thereby providing the patient's ankle with a degree of freedom in addition to the flexion and extension provided by the pivoting between the bearing component 36 and the dome portion 126. More particularly, as illustrated in FIGS. 7 and 8, the dome portion 126 is pivotable in the directions indicated by arrows 150, 152 relative to the base portion 127. Thus, relative pivoting motion between the dome portion 126 and the base portion 127 is enabled. The plane of pivoting in directions 150, 152 is perpendicular to the plane of flexion and extension indicated in FIG. 6. The plane of pivoting in directions 150, 152 is parallel to the medial-lateral axis 102. Moreover, the plane of pivoting in directions 150, 152 is substantially parallel to a plane 154 defined by a sole 156 (FIG. 9) of the right foot, as best seen in FIG. 2. It is also possible for the plane of pivoting in directions 150, 152 to be oriented at an angle of up to approximately 20 degrees relative to the plane 154.

The projection 144 of the base portion 127 is rotatable within the recess 131 of the dome portion 126 to thereby enable the pivoting. Both the inferior side 130 of the dome portion 126 and the superior side 140 of the plate 138 are planar with the exceptions of the recess 131 and the projection 144 in order to minimize a gap 160 therebetween and still enable relative rotation therebetween. Both the inferior side 130 and the superior side 140 are parallel to the plane of pivoting in directions 150, 152. The range of pivoting of the dome portion 126 in directions 150, 152 is approximately 30 degrees and is limited by the stretch and tightness of the ligaments that connect the fibula and tibia, the ankle bones, and the bones of the foot. By the projection 144 being received in the recess 131, relative movement between the dome portion 126 and the base portion 127 along both the medial-lateral axis 102 and an anterior-posterior axis 158 is inhibited.

Figure 10:
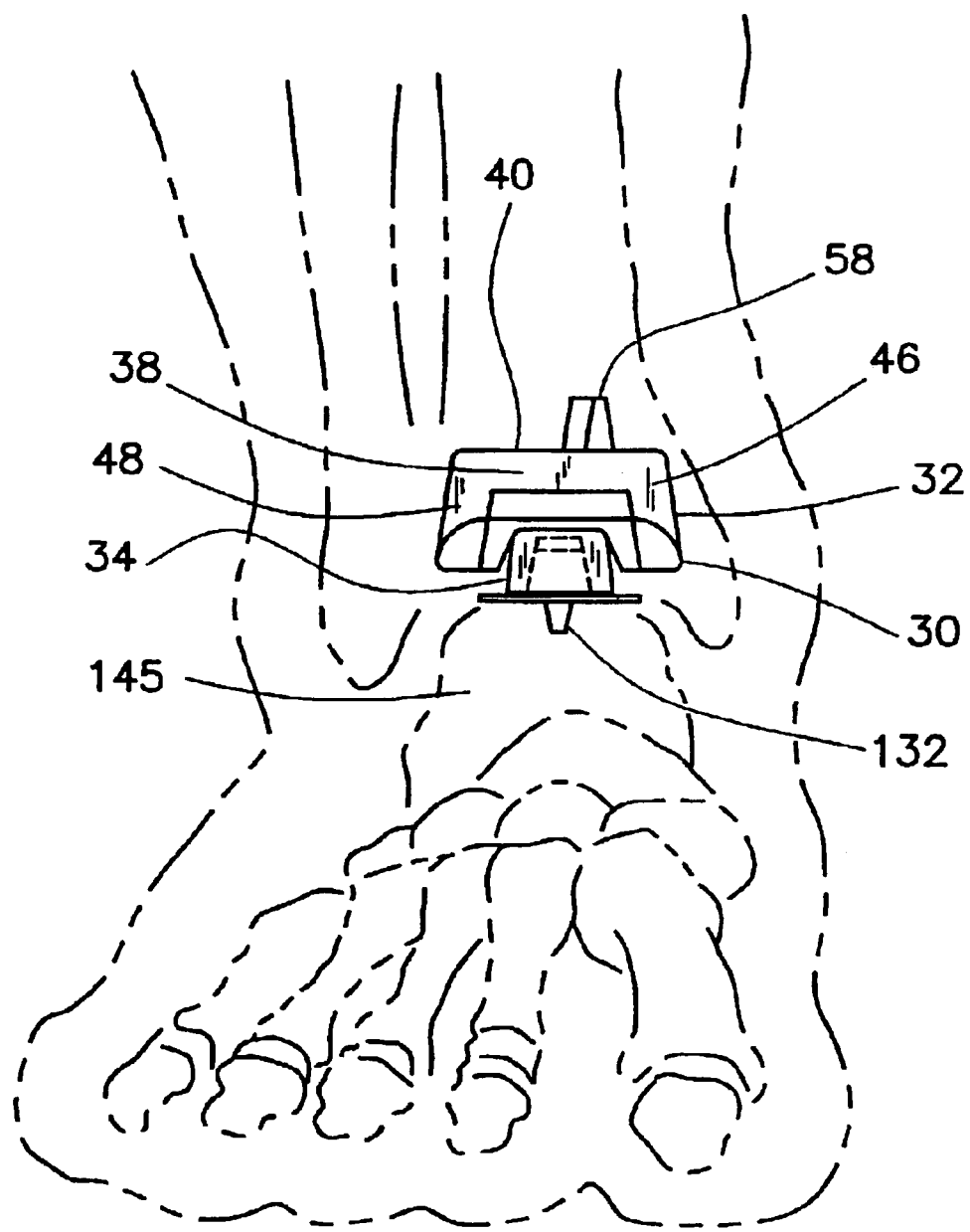
FIG. 10 is a front view of the ankle prosthesis of FIG. 1 implanted in a patient's ankle.

The tibial component 38 must be wide enough to bridge the area between the tibia and the fibula, as shown in FIG. 10. When implanted, the lateral wall 48 butts up against the fibula while the medial wall 46 butts up against the medial malleolus. In this manner, the fibula fuses to the tibia and a portion of the weight bearing is transferred to the fibula. An inferior surface 133 of the extension 56 is supported by bone, thereby inhibiting migration of the tibial assembly 32 in the superior-to-inferior direction 50. The superior wall 40 should be as thin as possible to minimize bone removal for implantation while maintaining sufficient strength to withstand the forces to which it is subjected.

As shown in FIG. 10, the ankle prosthesis 30 is implanted with the talar assembly 34 attaching to the talus 145 and the tibial assembly 32 attaching to the tibia and fibula bones with the superior wall 40 bridging the bones. The tibial fin 58 extends up into the tibia bone when implanted and positions the tibial component 38 correctly. In a similar manner, the talar fin 132 extends down into the talus 145 to keep the base portion 127 properly aligned when implanted. The ankle prosthesis 30 can be implanted with or without the use of bone cement.

During use, the patient may flex and extend his ankle, thereby causing the talar assembly 34 to pivot relative to the tibial assembly 32. More particularly, the dome portion 126 pivots, as illustrated in FIG. 6, within the bearing component 36. The patient may also turn his foot from side to side, thereby causing the base portion 127 of the talar assembly 34 to pivot relative to the dome portion 126, the tibial assembly 32, and the patient's fibula and tibia. More particularly, the projection 144 of the base portion 127 rotates within the recess 131 of the dome portion 126, as illustrated in FIGS. 7 and 8. If the patient pivots the anterior portion of his foot to the left, then the dome portion 126 rotates in direction 150 relative to the base portion 127 and the talus 145, as shown in FIG. 7. Conversely, if the patient pivots the anterior portion of his foot to the right, then the dome portion 126 rotates in direction 152 relative to the base portion 127 and the talus 145, as shown in FIG. 8.

In the embodiment discussed above, the base portion 127 and the dome portion 126 are shown as having a mating projection 144 and recess 131 to enable rotation therebetween. It is to be understood, however, that it is also possible for the base portion to have a recess and the dome portion to have a mating projection received in the recess. Further, it is also possible for the base portion and the dome portion to include other complementary structures that allow rotation therebetween. For example, the base portion can include an annular ring, and the dome portion can include a complementary annular groove to receive the ring and enable rotation between the base portion and the dome portion.

The tibial component and the talar assembly of the ankle prosthesis can be formed of conventional bio-compatible metals or suitably strong materials. For instance, the tibial component can be formed of a titanium alloy and the talar assembly can be formed of a cobalt-chromium alloy or stainless steel alloy. The bearing component can be made of a durable polyethylene. However, the tibial assembly and/or the talar assembly can be made of other materials having characteristics similar to those of the materials described above.

The tibial component and the talar assembly can be porous coated depending upon the preferred application. The tibial assembly and the talar assembly can be provided in various sizes and shapes to accommodate various patient ankle sizes and shapes.

In one preferred embodiment, the ankle prosthesis is provided to the orthopaedic surgeon in a kit of various sizes, dimensions and/or shapes of tibial assemblies and talar assemblies. The kit can include all of the components necessary to perform any replacement surgery described above. The components can be assembled in the operating room, if necessary.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An ankle prosthesis, comprising:
   an upper talar component including (i) a superior side having a first bearing surface, and (ii) an inferior side having an inferior surface, and (iii) a recess defined by an interior recess surface, said recess being accessible through an opening defined in said inferior surface;
   a lower talar component including (i) a superior side defining a superior surface, (ii) a projection extending from said superior surface, and (ii) an inferior side configured to be attached to a talus; and
   a tibial device having (i) a superior side configured to be attached to a tibia, and (ii) an inferior side having a second bearing surface supported on said first bearing surface of said upper talar component;
   wherein said upper talar component is pivotable in relation to said lower talar component,
   wherein said interior recess surface of said upper talar component is supported on said projection of said lower talar component during pivoting of said upper talar component in relation to said lower talar component, and
   wherein said inferior surface of said upper talar component is spaced apart from superior surface of said lower talar component during pivoting of said upper talar component in relation to said lower talar component.

2. The ankle prosthesis of claim 1, wherein:
   said projection defines a pivot axis, and
   said upper talar component pivots in relation to said lower talar component about said pivot axis.

3. The ankle prosthesis of claim 1, wherein:
   said inferior surface of said upper talar component extends from a first anterior end to a first posterior end,
   said superior surface of said lower talar component extends from a second anterior end to a second posterior end,
   said first anterior end is spaced apart from said second anterior end during pivoting of said upper talar component in relation to said lower talar component, and said first posterior end is spaced apart from said second posterior end during pivoting of said upper talar component in relation to said lower talar component.

4. The ankle prosthesis of claim 3, wherein said first bearing surface of said upper talar component extends from said first anterior end to said first posterior end.

5. The ankle prosthesis of claim 1, wherein:
said first bearing surface possesses one of a convex shape and a concave shape, and
said second bearing surface possesses the other of said convex shape and said concave shape.

6. The ankle prosthesis of claim 1, wherein:
said projection possesses a frustoconical shape, and
said recess possesses a complementary frustoconical shape.

7. The ankle prosthesis of claim 1, wherein:
said interior recess surface includes (i) a recess sidewall surrounding said opening defined in said inferior surface, and (ii) a recess ceiling spaced apart from said opening, and
said recess sidewall of said upper talar component is supported on said projection of said lower talar component during pivoting of said upper talar component in relation to said lower talar component.

8. The ankle prosthesis of claim 7, wherein said recess ceiling is spaced apart from said projection during pivoting of said upper talar component in relation to said lower talar component.

9. The ankle prosthesis of claim 1, wherein cooperation of said projection and said interior recess surface prevents any linear movement of said upper talar component in relation to said lower talar component when said projection is positioned within said recess.

10. The ankle prosthesis of claim 1, wherein:
said inferior surface of said upper talar component lies in a first plane,
said superior surface of said lower talar component lies in a second plane, and
said first plane is spaced apart from said second plane during pivoting of said upper talar component in relation to said lower talar component.

11. An ankle prosthesis, comprising:
an upper talar component including (i) a superior side having a first bearing surface, and (ii) an inferior side having an inferior surface, and (iii) a recess defined by an interior recess surface, said recess being accessible through an opening defined in said inferior surface;
a lower talar component including (i) a superior side defining a superior surface, (ii) a projection extending from said superior surface, and (ii) an inferior side configured to be attached to a talus; and
a tibial device having (i) a superior side configured to be attached to a tibia, and (ii) an inferior side having a second bearing surface supported on said first bearing surface of said upper talar component,
wherein said upper talar component is pivotable in relation to said lower talar component, and
wherein cooperation of said projection and said interior recess surface prevents any linear movement of said upper talar component in relation to said lower talar component when said projection is positioned within said recess.

12. The ankle prosthesis of claim 11, wherein:
said projection defines a pivot axis, and
said upper talar component pivots in relation to said lower talar component about said pivot axis.

13. The ankle prosthesis of claim 11, wherein:
said inferior surface of said upper talar component extends from a first anterior end to a first posterior end,
said superior surface of said lower talar component extends from a second anterior end to a second posterior end,
said first anterior end is spaced apart from said second anterior end during pivoting of said upper talar component in relation to said lower talar component, and
said first posterior end is spaced apart from said second posterior end during pivoting of said upper talar component in relation to said lower talar component.

14. The ankle prosthesis of claim 13, wherein said first bearing surface of said upper talar component extends from said first anterior end to said first posterior end.

15. The ankle prosthesis of claim 11, wherein:
said first bearing surface possesses one of a convex shape and a concave shape, and
said second bearing surface possesses the other of said convex shape and said concave shape.

16. The ankle prosthesis of claim 11, wherein:
said projection possesses a frustoconical shape, and
said recess possesses a complementary frustoconical shape.

17. The ankle prosthesis of claim 11, wherein:
said interior recess surface includes (i) a recess sidewall surrounding said opening defined in said inferior surface, and (ii) a recess ceiling spaced apart from said opening, and
said recess sidewall of said upper talar component is supported on said projection of said lower talar component during pivoting of said upper talar component in relation to said lower talar component.

18. The ankle prosthesis of claim 17, wherein said recess ceiling is spaced apart from said projection during pivoting of said upper talar component in relation to said lower talar component.

19. The ankle prosthesis of claim 11, wherein:
said inferior surface of said upper talar component lies in a first plane,
said superior surface of said lower talar component lies in a second plane, and
said first plane is spaced apart from said second plane during pivoting of said upper talar component in relation to said lower talar component.

20. The ankle prosthesis of claim 11, wherein:
said interior recess surface defines a third bearing surface,
an outer surface of said projection defines a fourth bearing surface, and
said third bearing surface contacts said fourth bearing surface during pivoting of said upper talar component in relation to said lower talar component.

* * * * *